US012527708B2

(12) United States Patent
Hirschbeck

(10) Patent No.: US 12,527,708 B2
(45) Date of Patent: Jan. 20, 2026

(54) ANATOMICALLY ADAPTABLE HEADREST APPARATUS

(71) Applicant: Christian Hirschbeck, Munich (DE)

(72) Inventor: Christian Hirschbeck, Munich (DE)

( * ) Notice: Subject to any disclaimer, the term of this patent is extended or adjusted under 35 U.S.C. 154(b) by 960 days.

(21) Appl. No.: 17/714,198

(22) Filed: Apr. 6, 2022

(65) Prior Publication Data

US 2023/0320916 A1 Oct. 12, 2023

(51) Int. Cl.

*A61G 15/12* (2006.01)
*A61N 2/00* (2006.01)
*A61N 2/02* (2006.01)

(52) U.S. Cl.

CPC ........... *A61G 15/125* (2013.01); *A61N 2/006* (2013.01); *A61N 2/02* (2013.01); *A61G 2210/00* (2013.01)

(58) Field of Classification Search

CPC ........ A61N 2/006; A61N 2/02; A61G 15/125; A61G 2210/00
USPC ................ 5/621, 636, 637; 600/13; 128/845
See application file for complete search history.

(56) References Cited

U.S. PATENT DOCUMENTS 4,213,213 A * 7/1980 Burnett .............. A61G 7/05753 5/655.4
5,121,756 A * 6/1992 Koledin .............. A61F 5/05833 128/DIG. 20
5,370,117 A * 12/1994 McLaurin, Jr. ........ A61B 6/501 378/68
6,374,439 B2 * 4/2002 Heimbrock ............ A61G 13/12 5/655.4
7,651,459 B2 * 1/2010 Cameron ................ A61N 2/02 600/9
8,555,439 B2 * 10/2013 Soto ..................... A61G 13/101 128/869
8,893,333 B2 * 11/2014 Soto ..................... A61G 13/101 5/636
10,639,491 B2 * 5/2020 Wölfel ..................... A61N 2/02
2010/0113959 A1 * 5/2010 Pascual-Leone ...... A61N 2/008 600/13
2010/0229306 A1 * 9/2010 Reeder, Jr. ............ A61G 7/072 5/643
2014/0276182 A1 * 9/2014 Helekar ............... A61B 5/4064 600/15
2015/0202453 A1 * 7/2015 Topp ...................... A61N 2/006 600/15
2016/0015588 A1 * 1/2016 Tamiya .................. A61B 90/14 128/845
2017/0291037 A1 * 10/2017 Tamiya ................ A61N 1/0529

* cited by examiner

*Primary Examiner* — David R Hare

(57) ABSTRACT

The present disclosure provides a headrest for therapeutic environments which is able to adapt and conform to the individual anatomic shape of a patient's head to provide firm support in a desired position for the duration of a therapy session, and which is able to maintain that shape to provide consistent positioning of a patient's head across multiple sessions. The headrest comprises an adjustable support element coupled to a headrest shell, with a headrest cushion being affixed to the shell that can conform to the shape of the patient's head and neck. The cushion is either a vacuum cushion or formed of a memory material, such that the deformation caused by supporting the patient can be reproduced if necessary.

10 Claims, 4 Drawing Sheets

ANATOMICALLY ADAPTABLE HEADREST APPARATUS

FIELD OF INVENTION

The present invention relates generally to headrests for therapeutic settings. More specifically, the present invention relates to an anatomically adaptable headrest for patients undergoing transcranial magnetic stimulation.

BACKGROUND

Transcranial magnetic stimulation, or TMS, is a non-invasive method for influencing brain activity by means of strong magnetic pulses. It is used, for example, in the therapy of depression. In TMS therapy, a stimulation coil is placed on a selected area of the head and remains there for the duration of the session, which is approximately 30 minutes.

A major problem with this procedure is the patient's head movements, which make it difficult to stably maintain the position of the coil at the stimulation site. This can both lead to ineffective therapy and cause the patient to experience headaches as a result of the prolonged tension in the neck and head muscles each session. Such headaches have become a relatively common side effect of TMS treatment.

Current solutions to this problem utilise standard head and neck supports attached therapy chairs, sometimes in combination with bolsters and/or support arms for leaning the head on its side.

In some cases, vacuum cushions are also placed around the patient's neck to provide a more comfortable sitting position during treatment. However, these solutions are not adapted to the individual anatomy/shape of the head of each respective patient, and thus cannot ensure stable positioning of the head without the patient also making an effort to support themselves in unnatural positions. For the same reasons, they also do not enable a reproducible position of the head across different sessions.

Other solutions of note include the use of chin straps/head straps that secure the patient to the chair. However, this is extremely dangerous, as the head of the patient is firmly held in place and cannot be pulled free by their own volition, which can lead to serious injury in the event of an epileptic seizure, which is a possible side effect of TMS.

It is within this context that the present invention is provided.

SUMMARY

The present disclosure provides a headrest for therapeutic environments which is able to adapt and conform to the individual anatomic shape of a patient's head to provide firm support in a desired position for the duration of a therapy session, and which is able to maintain that shape to provide consistent positioning of a patient's head across multiple sessions. The headrest comprises an adjustable support element coupled to a headrest shell, with a headrest cushion being affixed to the shell that can conform to the shape of the patient's head and neck. The cushion is either a vacuum cushion or formed of a memory material, such that the deformation caused by supporting the patient can be reproduced if necessary.

Thus, according to one aspect of the present disclosure there is provided a headrest apparatus, comprising: a support element, the support element comprising an adjustable slider having a first end configured for coupling to a therapeutic chair and an opposing second end, the angle and separation between the first end and the second end being adjustable; a headrest shell affixed to the second end of the support element, the shell comprising a curved rigid plate having first and second arms extending outwards from a central portion to form a concave surface, the shell thus being shaped to accommodate and support the neck and head of a person.

The headrest further comprising a headrest cushion affixed to the concave surface of the headrest shell, the cushion comprising an upper head support portion, a pair of side support arms extending outwards from the head support portion, and a lower neck and shoulder support portion encompassing the head support portion and side support arms, wherein the headrest cushion is configured to adapt and conform to the anatomical shape of a person who rests their head and neck against it.

In some embodiments, the headrest cushion is a vacuum cushion comprising a gas-impermeable outer cover, a valve for inflation and deflation, and a filling material, the cushion thus being configured to conform solidly about the head, neck, and shoulders of a person resting on it when evacuated from a deflated or semi-inflated state.

The filling may comprise expanded polystyrene beads. The valve may be located on an outer surface of one of the side support arms, the head support portion, or the neck and shoulder support portion.

In other embodiments, the cushion is formed of a memory foam material that will return to the anatomical shape it originally conformed to in response to a stimulus.

In some embodiments, the headrest cushion is removable from the headrest shell.

In some embodiments, the headrest apparatus further comprises a holding element for a transcranial magnetic stimulation coil, the holding device being positioned to reach a desired stimulation site on a person's head prior to the headrest cushion conforming to their anatomical shape.

In some embodiments, the headrest apparatus further comprises a curved brace coupled between the second end of the support element and the headrest shell.

BRIEF DESCRIPTION OF THE DRAWINGS

Various embodiments of the invention are disclosed in the following detailed description and accompanying drawings.

Figure 1:
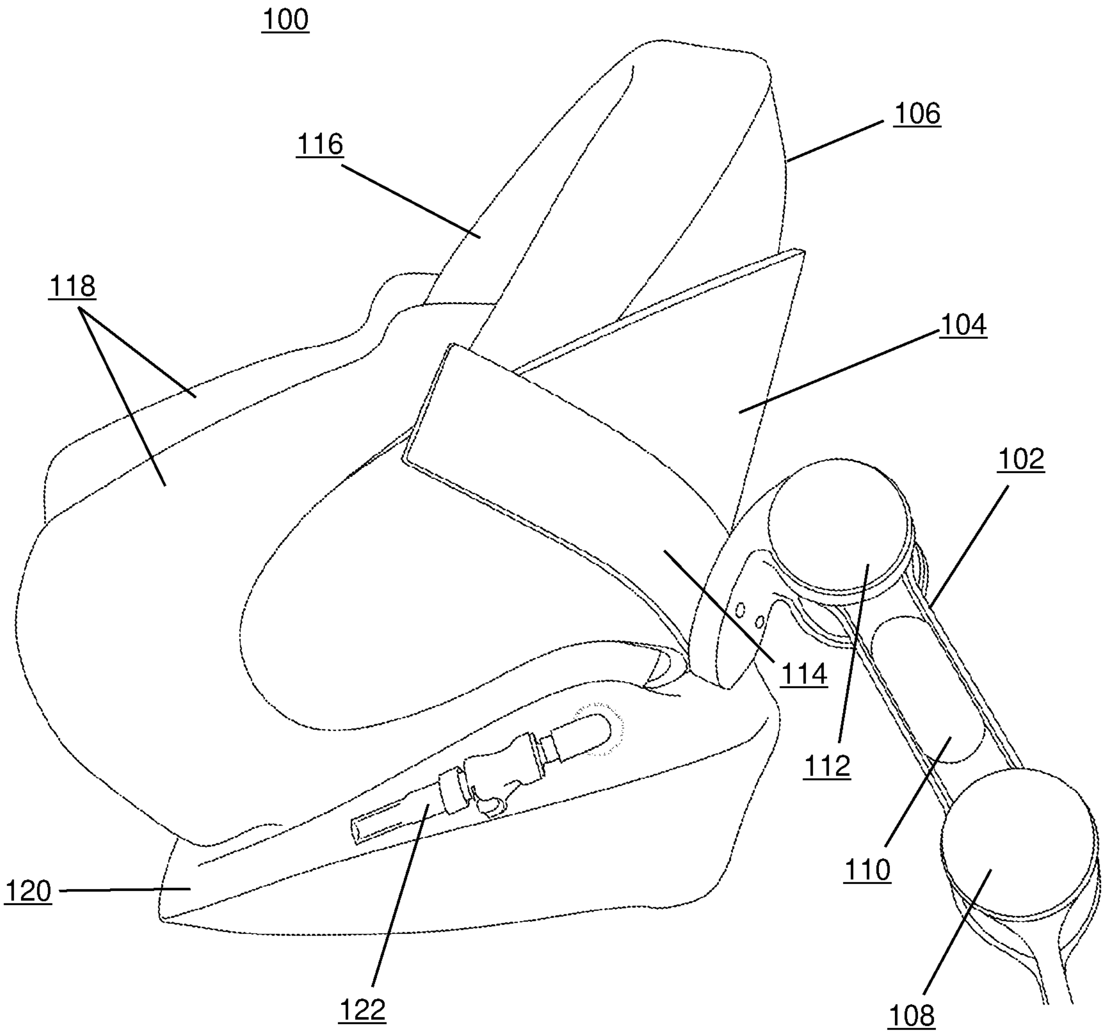
FIG. 1 illustrates an isometric view of an example configuration of the anatomically adaptable headrest apparatus of the present disclosure with the headrest cushion in an inflated state.

Common reference numerals are used throughout the figures and the detailed description to indicate like elements. One skilled in the art will readily recognize that the above figures are examples and that other architectures, modes of operation, orders of operation, and elements/functions can be provided and implemented without departing from the characteristics and features of the invention, as set forth in the claims.

DETAILED DESCRIPTION AND PREFERRED EMBODIMENT

The following is a detailed description of exemplary embodiments to illustrate the principles of the invention. The embodiments are provided to illustrate aspects of the invention, but the invention is not limited to any embodiment. The scope of the invention encompasses numerous alternatives, modifications and equivalent; it is limited only by the claims.

Numerous specific details are set forth in the following description in order to provide a thorough understanding of the invention. However, the invention may be practiced according to the claims without some or all of these specific details. For the purpose of clarity, technical material that is known in the technical fields related to the invention has not been described in detail so that the invention is not unnecessarily obscured.

The terminology used herein is for the purpose of describing particular embodiments only and is not intended to be limiting of the invention. As used herein, the term "and/or" includes any combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Referring to FIG. 1, an isometric view of an example configuration of the anatomically adaptable headrest apparatus 100 is shown.

As can be seen, the headrest is comprised of an adjustable support element 102 that connects to a therapeutic chair, a headrest shell 104 which provides a structural support at the upper end of the support element, and a deformable headrest cushion 106 that is configured to conform around and provide support to the shoulders, neck, and head of a patient without actually constricting their movement such that they would be prevented from moving away from the headrest should they suffer a seizure.

The support element of the present example consists of an adjustable slider 110 mounted between two hinged joints 108 and 112, that allow the support element to be adjusted both in length and in angle to accommodate patients and chairs of different shapes and sizes. In the present example, a curved brace 114 is affixed to the upper hinged joint 112 which couples to and supports the headrest shell 104. In other examples the support element may be directly coupled to the headrest shell 104.

The headrest shell 104 is a curved rigid plate having first and second arms extending outwards from a central portion and away from the brace to form a concave surface that is the structural support for the headrest cushion that the patient leans back into.

The headrest cushion 106 rests against and is coupled firmly to the headrest shell 104, and is shaped to provide support to the shoulders, neck, and head of the patient. The cushion can be formed various ways, but it is important that it can conform to, and reproduce the shape of, the individual anatomy of the patient resting on it. Thus various types of memory foam materials that regain a previous shape in response to stimuli such as heat, force, etc would be suitable. In the present example however, the headrest cushion is formed of a vacuum cushion.

Vacuum cushions for positioning patients for various radiation therapy procedures are well known and widely used. These cushions are comprised of several common elements: a gas-impermeable outer cover, valve-stem with closable valve, and a filling such as expanded polystyrene beads. In use, the patient is positioned on the cushion while it is in its semi-inflated or loose state. A source of vacuum, usually a vacuum pump, is attached to the closable valve. As the cushion is evacuated, the expanded filling (i.e. the polystyrene beads) is forced together to form a rigid support that conforms to the body contour of the patient. The expanded polystyrene beads may be bunched-up around a portion of the patient's anatomy so that when the beads become rigid they will hold that portion of the patient's anatomy in the desired position.

The headrest cushion 106 is affixed to the concave surface of the headrest shell 104, an comprises an upper head support portion 116, a pair of side support arms 118 extending outwards from the head support portion, and a lower neck and shoulder support portion 120 encompassing the head support portion and side support arms. A valve 122 is disposed on the impermeable outer membrane to allow the removal of air to transition between semi-inflated and rigid supporting states.

Figure 2:
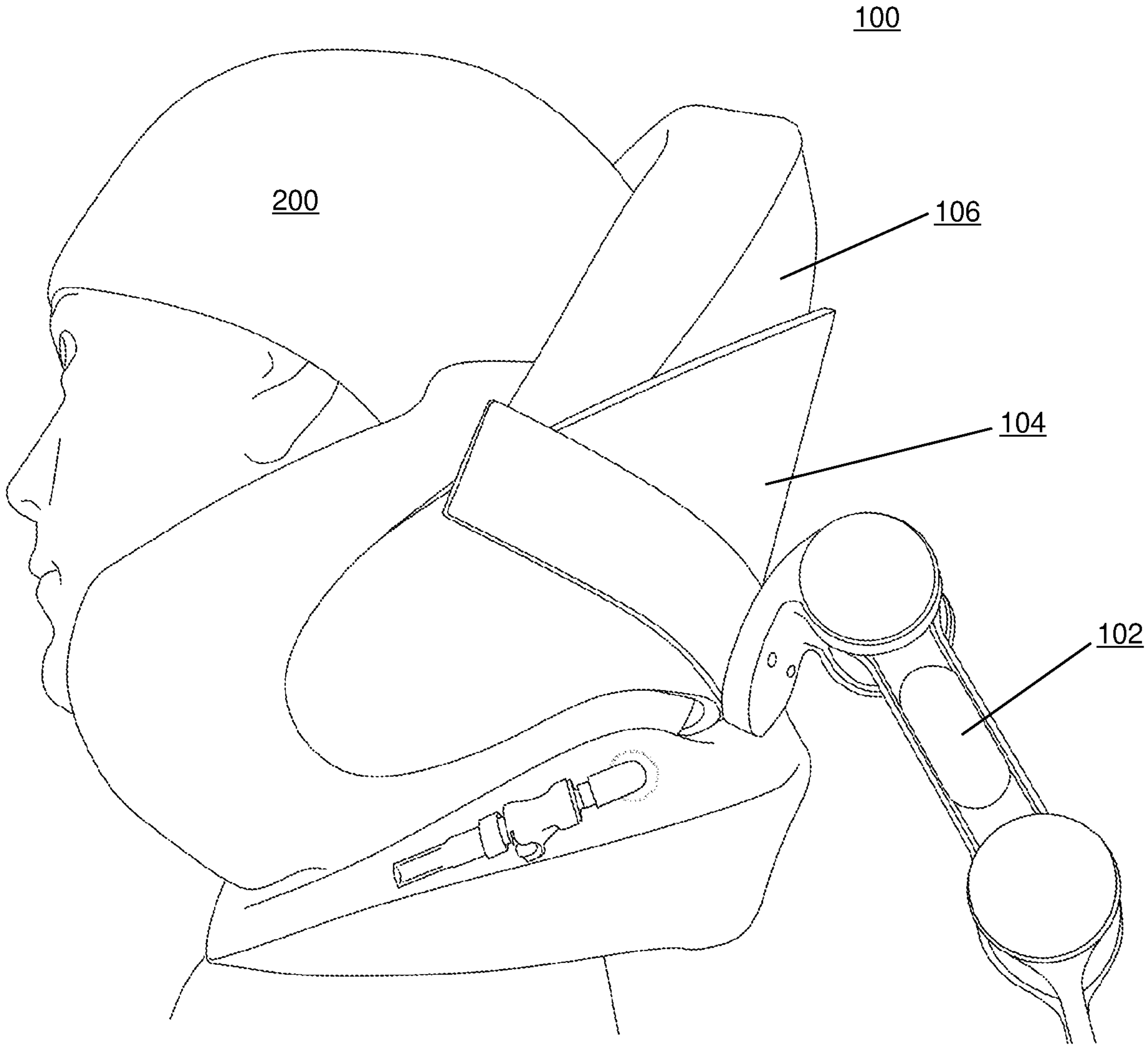
FIG. 2 illustrates an isometric view of the example configuration with a patient resting their head and neck in the headrest cushion.

Referring to FIG. 2, an isometric view of the example configuration is shown with a patient 200 resting their head and neck in the headrest cushion 106.

In use, the patient sits in the therapeutic chair and the support element 102 is adjusted to the patient's height and position. The patient can then place the head back against the vacuum cushion so that it encloses the back of the head, neck, and both sides of the head up to the ears. With the use of a pump, air can be extracted through the valve 122, solidifying the cushion. The cushion then conforms to maintains the individual anatomical shape of the patient's head and neck, limiting their movement but allowing them to pull free if needed. The anatomically adapted shape of the cushion also relieves pressure on the neck and prevents a stiff head position during the therapy session.

The headrest cushion 106 may be removable from the headrest shell such that a particular cushion can be saved for a particular patient to retain a consistent position and shape between therapy sessions without having to conform to their anatomy at the beginning of each session.

Figure 3:
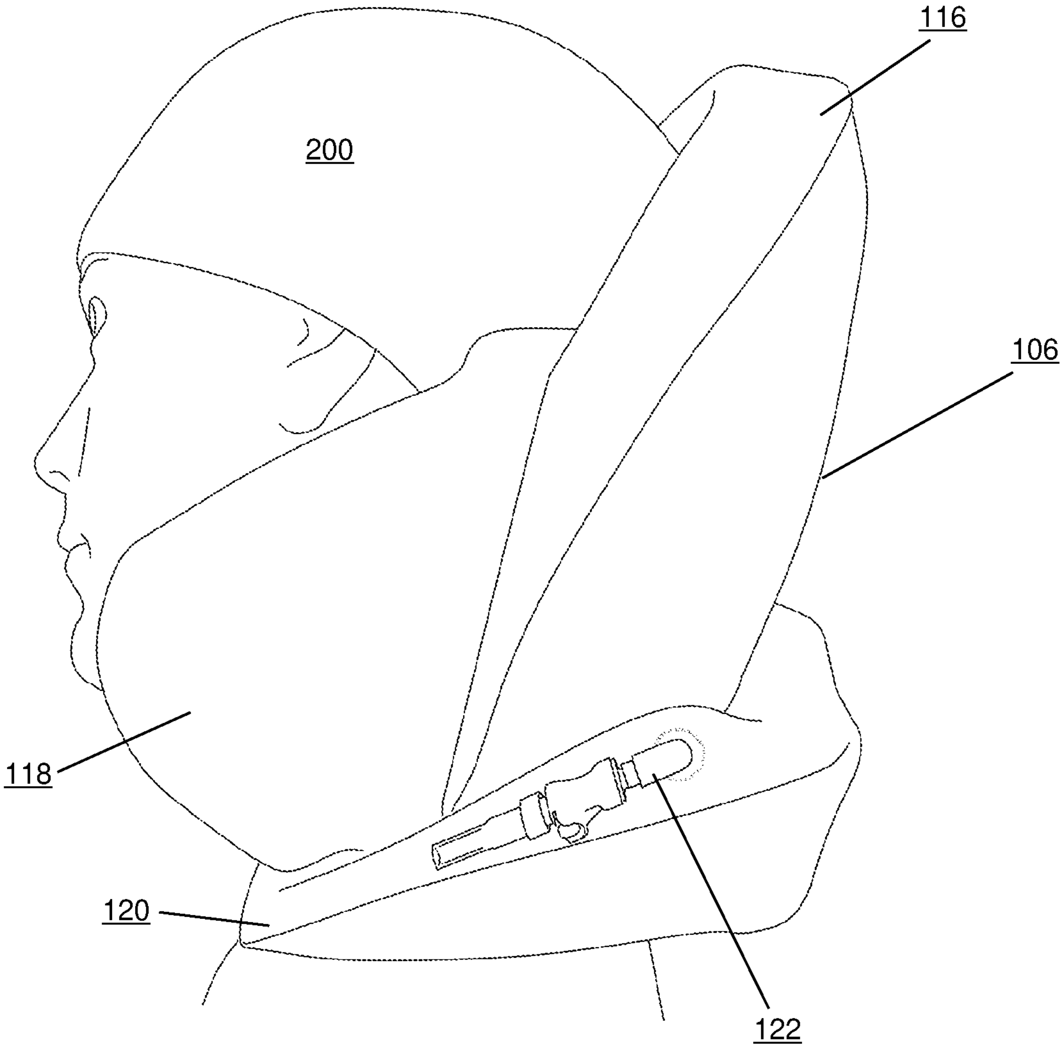
FIG. 3 illustrates an isometric view of the headrest cushion of the example configuration having conformed about the patient's anatomical shape and removed from the support element and headrest shell.

Referring to FIG. 3 illustrates an isometric view of the headrest cushion 106 is shown having conformed about the patient's anatomical shape and removed from the support element and headrest shell.

It should be noted that the valve 122 can be positioned at any desired point on the exterior surface of the impermeable membrane of the cushion 106.

Figure 4:
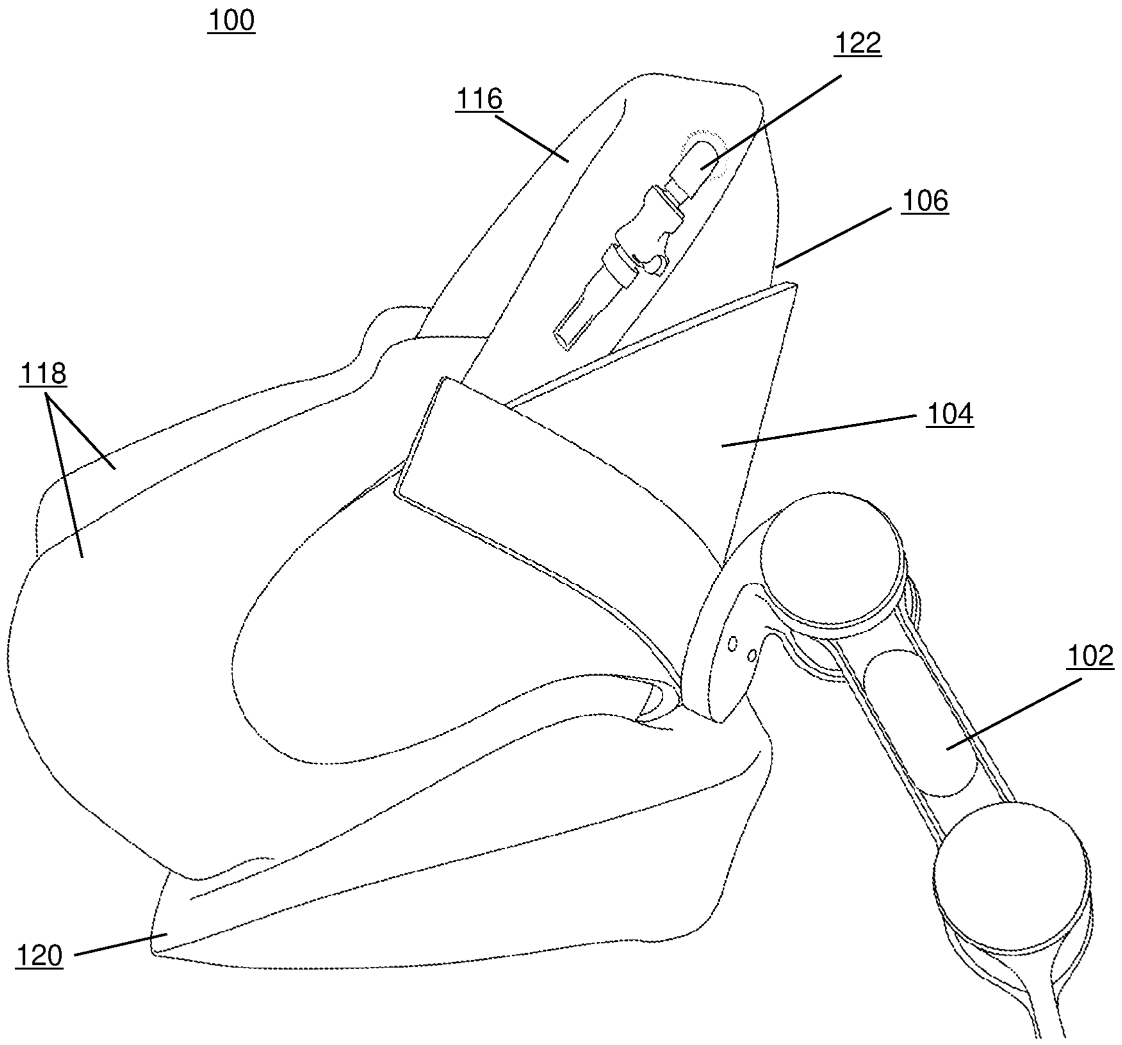
FIG. 4 illustrates an isometric view of an alternative configuration of the anatomically adaptable headrest apparatus of the present disclosure with the valve for the headrest cushion located on the head support portion.

Referring to FIG. 4, an isometric view is shown of an alternative configuration of the headrest apparatus 100 with the valve 122 located on the head support portion 116 of the cushion.

Furthermore, although not illustrated, it is noted that the headrest apparatus may be extended to further comprise a holding element for a transcranial magnetic stimulation coil, the holding device being positioned to reach a desired stimulation site on a person's head prior to the headrest cushion conforming to their anatomical shape.

Unless otherwise defined, all terms (including technical terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

The disclosed embodiments are illustrative, not restrictive. While specific configurations of the anatomically adaptable headrest have been described in a specific manner referring to the illustrated embodiments, it is understood that the present invention can be applied to a wide variety of solutions which fit within the scope and spirit of the claims. There are many alternative ways of implementing the invention.

It is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. An anatomically adaptable headrest apparatus, the headrest apparatus, comprising:

a support element, the support element comprising an adjustable slider having a first end configured for coupling to a therapeutic chair and an opposing second end, the adjustable slider being configured for both angular and linear adjustment between the first and second ends to selectively position the second end relative to the therapeutic chair;

a headrest shell affixed to the second end of the support element, the headrest shell comprising a curved rigid plate having first and second arms extending outwards from a central portion to form a concave interior surface, the headrest shell thus being shaped to accommodate and support a neck and a head of a person; and a headrest cushion removably secured to the concave interior surface of the headrest shell, the headrest cushion comprising an upper head support portion, a pair of lateral side support arms extending outwards from the head support portion, and a neck and shoulder support portion encompassing the head support portion and lateral side support arms, wherein the headrest cushion comprises a material that conforms to and retains the anatomical contour of the head, neck, and shoulders when compressed against the headrest shell, and wherein the headrest shell mechanically constrains deformation of the cushion to maintain a reproducible positioning surface for a transcranial magnetic stimulation (TMS) procedure;

wherein a curved brace is affixed to an upper hinged joint and is configured to couple to and support the headrest shell.

2. The headrest apparatus according to claim 1, wherein the headrest cushion is a vacuum cushion comprising a gas-impermeable outer cover, a valve for inflation and deflation, and a filling material, the cushion thus being configured to conform solidly about the head, neck, and shoulders of a person resting on the headrest cushion when evacuated from a deflated or semi-inflated state.

3. The headrest apparatus according to claim 2, wherein the filling comprises expanded polystyrene beads.

4. The headrest apparatus according to claim 2, wherein the valve is located on an outer surface of one of the lateral side support arms.

5. The headrest apparatus according to claim 2, wherein the valve is located on the head support portion.

6. The headrest apparatus according to claim 2, wherein the valve is located on the neck and shoulder support portion.

7. The headrest apparatus according to claim 1, wherein the headrest cushion is formed of a memory foam material that will return to the anatomical shape the headrest cushion originally conformed to in response to a stimulus.

8. The headrest apparatus according to claim 1, wherein the headrest cushion is removable from the headrest shell.

9. The headrest apparatus according to claim 1, wherein the headrest apparatus further comprises a holding element for a transcranial magnetic stimulation coil, the holding device being positioned to reach a desired stimulation site on a person's head prior to the headrest cushion conforming to their anatomical shape.

10. The headrest apparatus according to claim 1, wherein the headrest apparatus further comprises the curved brace coupled between the second end of the support element and the headrest shell.

* * * * *